US009355547B2

(12) United States Patent
Stevens et al.

(10) Patent No.: US 9,355,547 B2
(45) Date of Patent: May 31, 2016

(54) IDENTIFYING A CHANGE IN A HOME ENVIRONMENT

(71) Applicant: International Business Machines Corporation, Armonk, NY (US)

(72) Inventors: Mark B. Stevens, Austin, TX (US); John D. Wilson, Houston, TX (US)

(73) Assignee: International Business Machines Corporation, Armonk, NY (US)

( * ) Notice: Subject to any disclaimer, the term of this patent is extended or adjusted under 35 U.S.C. 154(b) by 66 days.

(21) Appl. No.: 14/284,581

(22) Filed: May 22, 2014

(65) Prior Publication Data

US 2015/0339905 A1 Nov. 26, 2015

(51) Int. Cl.
G09B 21/00 (2006.01)
G08B 21/02 (2006.01)

(52) U.S. Cl.
CPC ...................... G08B 21/02 (2013.01)

(58) Field of Classification Search
CPC combination set(s) only.
See application file for complete search history.

(56) References Cited

U.S. PATENT DOCUMENTS

| | | | |
|---|---|---|---|
| 7,408,465 B2 | 8/2008 | Boss et al. | |
| 7,598,976 B2 | 10/2009 | Sofer et al. | |
| 8,605,141 B2 | 12/2013 | Dialameh et al. | |
| 2006/0129308 A1* | 6/2006 | Kates | A61H 3/061 701/532 |
| 2008/0143517 A1 | 6/2008 | Goffin | |
| 2010/0263603 A1* | 10/2010 | Baron | A01K 13/006 119/850 |
| 2012/0127291 A1 | 5/2012 | Mahoney | |
| 2013/0216093 A1* | 8/2013 | Lee | A61H 3/061 382/103 |
| 2013/0250078 A1* | 9/2013 | Levy | A61F 9/08 348/62 |
| 2013/0253818 A1* | 9/2013 | Sanders | G01C 21/206 701/419 |
| 2013/0332452 A1 | 12/2013 | Jarvis | |
| 2014/0040252 A1 | 2/2014 | Jarvis | |
| 2014/0112537 A1* | 4/2014 | Frank | H04N 5/33 382/103 |
| 2015/0116082 A1* | 4/2015 | Cregg | G07C 9/00309 340/5.61 |

FOREIGN PATENT DOCUMENTS

CN 102499862 A 6/2012
WO 2013186574 A2 12/2013

OTHER PUBLICATIONS

Anonymous, "Method for Implementation of a Location, Direction, Speed Based Smarter Notification Service", IP.com Prior Art Database Technical Disclosure. IP.com No. IPCOM000233241D, Published Dec. 3, 2013. 4 pages.

Barraud, E., "Mapping a Room in a Snap", Mediacom, Jun. 18, 2013. http://actu.epfl.ch/news/mapping-a-room-in-a-snap/.

(Continued)

*Primary Examiner* — Fekadeselassie Girma
*Assistant Examiner* — Thomas McCormack
(74) *Attorney, Agent, or Firm* — Jay Wahlquist; Isaac J. Gooshaw

(57) ABSTRACT

A system and computer implemented method for detecting a change in a home environment for a visually impaired user is disclosed. The method may include monitoring the home environment using a set of sensors configured to collect environment data for a set of areas of the home environment. The method may also include detecting an environmental change in an area of the home environment. The method may also include providing, in response to a triggering event, a notification of the environmental change.

11 Claims, 5 Drawing Sheets

(56) References Cited

OTHER PUBLICATIONS

Blum, J., et al., "What's around Me? Spatialized Audio Augmented Reality for Blind Users with a Smartphone", Mobile and Ubiquitous Systems: Computing, Networking, and Services. Lecture Notes of the Institute for Computer Sciences, Social Informatics and Telecommunications Engineering vol. 104, 2012, pp. 49-62. © Springer, Part of Springer Science+Business Media.

Coughlan, J., et al., "Cell Phone-based Wayfinding for the Visually Impaired", 15 pages.

Hollister, S., "OrCam's $2,500 augmented reality glasses speak words aloud, help the visually impaired 'see'", Jun. 5, 2013, 11:38 p.m. http://www.theverge.com/2013/6/5/4400990/orcam-g lasses-read-aloud.

IBM, "Environmental and Hazard Detection Using a Portable Apparatus", IP.com Prior Art Database Technical Disclosure. IP.com No. IPCOM000177547D, published Dec. 17, 2008. 3 pages.

Ivanchenko, V., et al., "Crosswatch: a Camera Phone System for Orienting Visually Impaired Pedestrians at Traffic Intersections", 7 pages.

Kim, et al., Usability and Design Guidelines of Smart Canes for Users with Visual Impairments, International Journal of Design, 2013. vol. 7, No. 1. pp. 99-110.

Swobodzinski, M., et al., "An indoor routing algorithm for the blind: development and comparison to a routing algorithm for the sighted", International Journal of Geographical Information Science. vol. 00, No. 00, Jun. 2008, pp. 1-28.

Tapu, R., et al., "A Computer Vision System that Ensure the Autonomous Navigation of Blind People", The 4th IEEE International Conference on E-Health and Bioengineering—EHB 2013. Grigore T. Popa University of Medicine and Phamacy. Iasi, Romania, Nov. 21-23, 2013. Copyright 2013 IEEE.

Unknown, "What is LookTel" LookTel.com 3 pages. http://www.looktel.com.

Yi, C., et al., "Finding Objects for Assisting Blind People", Network Modeling Analysis in Health Informatics and Bioinformatics. 13 pages.

List of Patents or Patent Applications Treated as Related.

\* cited by examiner

IDENTIFYING A CHANGE IN A HOME ENVIRONMENT

FIELD

The present disclosure relates to computer-aided navigation, and more specifically, identifying a change in a home environment for a visually impaired user.

BACKGROUND

Various methods and systems can aid visually impaired individuals in unfamiliar surroundings. Devices and systems may guide the visually impaired by utilizing detection devices to warn the user of obstacles. Such devices may allow for the user to navigate a home environment.

SUMMARY

Aspects of the present disclosure, in certain embodiments, are directed toward detecting a change in a home environment for a visually impaired user. In certain embodiments, the method may include monitoring the home environment using a set of sensors configured to collect environment data for a set of areas of the home environment. In certain embodiments, the method may include detecting an environmental change in an area of the home environment. In certain embodiments, the method may include providing, in response to a triggering event, a notification of the environmental change.

The above summary is not intended to describe each illustrated embodiment or every implementation of the present disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

Figure 1:
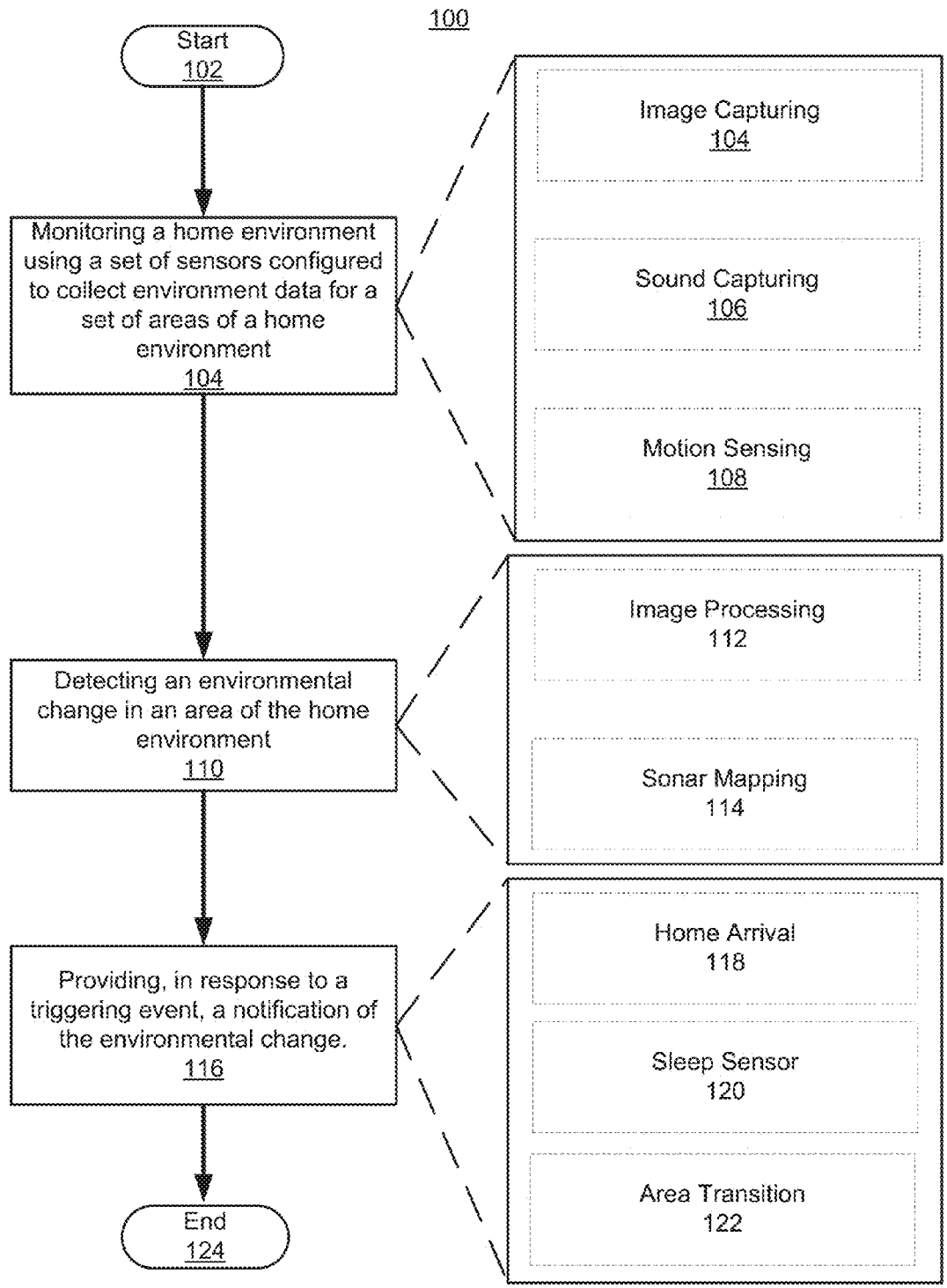
FIG. 1 illustrates a method for detecting a change in a home environment for a visually impaired user, according to embodiments.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

Aspects of the present disclosure relate to various embodiments of a system and method for detecting a change in a home environment for a visually impaired user. More particular aspects relate to using image processing, sonar mapping, and motion sensing systems to detect the change in the home environment for the visually impaired user. The method may include monitoring the home environment using a set of sensors configured to collect environment data for a set of areas of the home environment. The method may also include detecting an environmental change in an area of the home environment. Additionally, in certain embodiments, the method may include providing a notification of the environmental change. The notification of the environmental change may be provided in response to a triggering event.

For a visually impaired person, navigating from one location to another can pose a variety of challenges. If a visually impaired person is not familiar with an environment, there may be a number of obstacles that the he or she carefully maneuvers to arrive at his or her intended destination. When a visually impaired person is navigating a known environment (e.g., a home environment or location they are familiar with), he or she may memorize the location of objects and the number of steps from one location to another. However, aspects of the present disclosure relate to the recognition that, in certain situations, an unexpected obstacle in a home environment (e.g., a piece of furniture or other object that has been moved within the home) may be potentially hazardous to a visually impaired person, as he or she may not be on their guard for obstacles when traveling in a familiar environment. Accordingly, aspects of the present disclosure, in certain embodiments, relate to a system and method for monitoring a home environment using image processing, sonar mapping, and motion sensing systems, and detecting a potential obstacle. A notification of the potential obstacle may be provided to the user of the system. Aspects of the present disclosure may provide benefits associated with confidence, efficiency, and safety (e.g., faster and safer home environment navigation) for a visually impaired user.

Aspects of the present disclosure relate to various embodiments of a system and method for detecting a change in a home environment for a visually impaired user. More particular aspects relate to using image processing, sonar mapping, and motion sensing systems to detect the change in the home environment for the visually impaired user. The method and system may work on a number of devices and operating systems. Aspects of the present disclosure include monitoring a home environment using a set of sensors configured to collect environment data for a set of areas of the home environment. The set of sensors can include motion sensors, audio sensors, cameras, or other types of sensors. The method may also include detecting an environmental change in an area of the home environment. The environmental change may be a movement of an object (e.g., an object that may be an obstacle for a visually impaired user), a broken object, a substantial change in temperature, or another change that may affect the visually impaired user. The method may also include providing, in response to a triggering event, a notification of the environmental change.

In certain embodiments, collecting the environment data may include capturing, by an image capturing system, a first set of images for the set of areas of the home environment. In certain embodiments, detecting the environmental change in the area of the home environment includes capturing, in response to receiving a motion alert from a motion detection system coupled to the image capturing system, a second set of images for the set of areas. The method may then include identifying an object of the second set of images meeting an obstruction criteria. The obstruction criteria may include an object displacement threshold based on an origin position and a subsequent position, and an object size threshold based on a first dimension, a second dimension, and a third dimension. In certain embodiments, providing the notification of the environmental change may include notifying a user, using a mobile device communicatively connected to the image capturing system, of the identified object meeting the obstruction criteria in response to detecting a home arrival. In certain embodiments, the home arrival may be detected by a security system in response to a door unlock of a home. In certain embodiments, detecting the home arrival may include recording, by a sound capture device, a set of dog barks (including like noises, such as panting). In response to recording the set of dog barks, the method may include analyzing a bark frequency and a bark pitch of the set of dog barks. The method may include determining, based on the bark frequency and the bark pitch, occurrence of the home arrival.

In certain embodiments, collecting the environment data may include mapping, using a sonar mapping system, a first sonar map of the set of areas of the home environment. In certain embodiments, detecting the environmental change in the area of the home environment may include mapping, in response to receiving a noise alert from a sound detection system coupled to the sonar mapping system, a second sonar map of the set of areas. The method may also include identifying an object of the second sonar map meeting an obstruction criteria. In certain embodiments, providing the notification of the environmental change may include notifying, in response to an alert from a sleep sensor, using a mobile device communicatively connected to the image capturing system, a user of the identified object meeting the obstruction criteria. The alert from the sleep sensor may include a change in a pulse beyond a pulse threshold, and a change in a respiration frequency beyond a respiration threshold. In certain embodiments, the method may include collecting, by the sonar mapping system, a sound profile data including a background noise level of the set of areas. The method may also include creating, using sound profile data other than the background noise level, the sonar map.

In certain embodiments, collecting the environment data may include capturing, by an image capturing system, a first set of images for the set of areas of the home environment. In certain embodiments, detecting the environmental change in the area of the home environment includes capturing, in response to receiving a motion alert from a motion detection system coupled to the image capturing system, a second set of images for the set of areas. The method may then include identifying an object of the second set of images meeting an obstruction criteria. The obstruction criteria may include an object displacement threshold based on an origin position and a subsequent position, and an object size threshold based on a first dimension, a second dimension, and a third dimension. In certain embodiments, providing the notification of the environmental change may include notifying a user, using a mobile device communicatively connected to the image capturing system, of the identified object meeting the obstruction criteria in response to detecting an area transition. In certain embodiments, detecting the area transition may include monitoring the location of a cane of the user. The cane may be equipped with a RFID (radio-frequency identification) bit communicatively connected to a RFID tracking system. The method may also include detecting that the location of the cane has been displaced by a distance value greater than a distance threshold. In certain embodiments, detecting the area transition may include using a thermal imaging system to monitor a body heat signature. The method may also include detecting that the body heat signature has been displaced by a distance value greater than a distance threshold.

Turning now to the figures, FIG. 1 illustrates a method 100 for detecting a change in a home environment for a visually impaired user, consistent with various embodiments of the present disclosure. Aspects of FIG. 1 are directed toward using image capturing, sound capturing, and motion sensing systems to detect the change in the home environment for the visually impaired user. The method 100 may begin at block 102 and end at block 124. Consistent with various embodiments, the method 100 can include a monitoring block 104, an image capturing block 104, a sound capturing block 106, a motion sensing block 108, a detecting block 110, an image processing block 112, a sonar mapping block 114, a providing block 116, a home arrival block 118, a sleep sensor block 120, and an area transition block 122.

Consistent with various embodiments of the present disclosure, at block 104 the method 100 can include monitoring a home environment using a set of sensors configured to collect environment data for a set of areas of the home environment. The home environment may be a shelter or residence of a person, a family, or a household. In certain embodiments, the home environment may, for example, be a house, apartment, townhome, condominium, or other residence. The home environment may be equipped with a set of sensors configured to monitor the home environment. The set of sensors may include motion sensors, audio sensors, cameras, or other types of sensors that can collect data about the surrounding environment. The set of sensors may, in certain embodiments, be one or more household electronic devices stationed within the home that serve multiple functions. For example, the sensors may include webcams, televisions equipped to receive voice commands, phones, intercom systems, security cameras and microphones, stereos, and the like. In certain embodiments, the set of sensors may include specialized equipment including cameras, microphones, motion sensors, thermal imaging systems, RFID (radio-frequency identification) tracking systems, or other types of sensors.

In certain embodiments, the set of sensors may be equipped to collect environment data for a set of areas of the home environment. The environment data may be video, audio, thermal, motion, infrared, or other data containing information related to the home environment. For example, the environment data may be video footage or still images, captured sounds, heat signatures, or other data collected by the set of sensors. As shown in FIG. 1, in certain embodiments, monitoring the home environment can include image capturing 104, sound capturing 106, and motion sensing 108. At image capturing block 104, method 100 can include using an image capturing system (e.g., cameras, etc.) to capture a set of images of one or more areas of the home environment. At sound capturing block 106, the method 100 can include using a sound capturing system to collect sound and noise data for one or more areas of the home environment. At motion sensing block 108, the method 100 can include using a motion-sensing system to collect motion data for one or more areas of the home environment. The areas of the home environment may be one or more regions or subdivisions of the home environment. The subdivisions of the home environment may be based on physical constructions (e.g., walls, doors, etc.) or based on function (kitchen, dining room, living room, etc.). As an example, the areas of the home environment may include a bedroom, a kitchen, a living room, a bathroom, and the like.

Consistent with various embodiments, at block 110 the method 100 can include detecting an environmental change in an area of the home environment. The change in the home environment can be an alteration of the state of one or more aspects of the home environment. For example, the environmental change may be a temperature change beyond a threshold level, an object that has been added to or removed from an area of the home environment, a malfunction of an appliance, an unidentified person or animal, a noise, and the like. The change in the home environment can be detected in one of a number of ways. As shown in FIG. 1, detecting the change in the home environment can include image processing 112 and sonar mapping 114. At image processing block 112, the method 100 can include using image processing techniques (e.g., digital image analysis algorithms, object recognition techniques, etc.) to detect the change in the home environment. As an example, in certain embodiments, image processing techniques may be used to compare a first set of images of an area of the home environment to a second set of images of the area of the home environment. Accordingly, the method 100 can include detecting an environmental change such as an object from the second set of images that was not present in the first set of images. At block 114, the method 100 can include using sonar mapping techniques to create a sonar map of an area of the home environment. As an example, in certain embodiments, at block 114 the method 100 can include comparing a first sonar map of an area of the home environment to a second sonar map of an area of the home environment, and identifying an object in the second sonar map that was not present in the first sonar map.

Consistent with various embodiments, at block 116 the method 100 can include providing, in response to a triggering event, a notification of the environmental change. The notification of the environmental change may include informing a user of the time, location, and nature of the environmental change. Consistent with various embodiments, the notification of the environmental change may be provided in one of a number of ways. For example, the notification may be a voice message that is announced in one or more areas of the home environment via a speaker, intercom, stereo, television, radio, or other device. In certain embodiments, the notification of the environmental change may be provided via a mobile device of the user in the form of a voice message, text message, vibrate alert, or sound alert. The notification of the environmental change may be provided to the user in response to a triggering event. The triggering event may include an occurrence, trigger, or stimuli that can be detected by the set of sensors or other method. Consistent with embodiments of the present disclosure, the triggering event can include a home arrival 118, a sleep sensor 120, or an area transition 122. Other triggering events are also contemplated. In certain embodiments, the home arrival 118 can include detecting that a known user has arrived at the home environment. In certain embodiments, the sleep sensor 120 can be configured to detect when a user has awoken from sleeping, or arisen from bed. In certain embodiments, the area transition 122 can include detecting that a user has moved from one area (e.g., room) to another area of the home environment.

Aspects of the present disclosure, in certain embodiments, are directed toward monitoring the home environment in response to the triggering event. In certain embodiments, the set of sensors may be in a standby mode, and be configured to detect one of a number of triggering events. In certain embodiments, the triggering event may be a scheduled time trigger. Put differently, in certain embodiments, the set of sensors may be configured to monitor the home environment at a set of configurable time intervals. Consider the following example. The set of sensors may be configured to monitor the home environment for changes each hour of the day (e.g., on each hour). While a user who lives in the home environment is on vacation, another individual may enter the home environment at 11:04 AM to water one or more plants of the home environment. The individual may move one or more objects or pieces of furniture while watering the plants, and replace them in their original position before leaving the home environment at 11:49. At 12:00 PM, the set of sensors may monitor for a change in the home environment, and not detect a change in the home environment.

Figure 2:
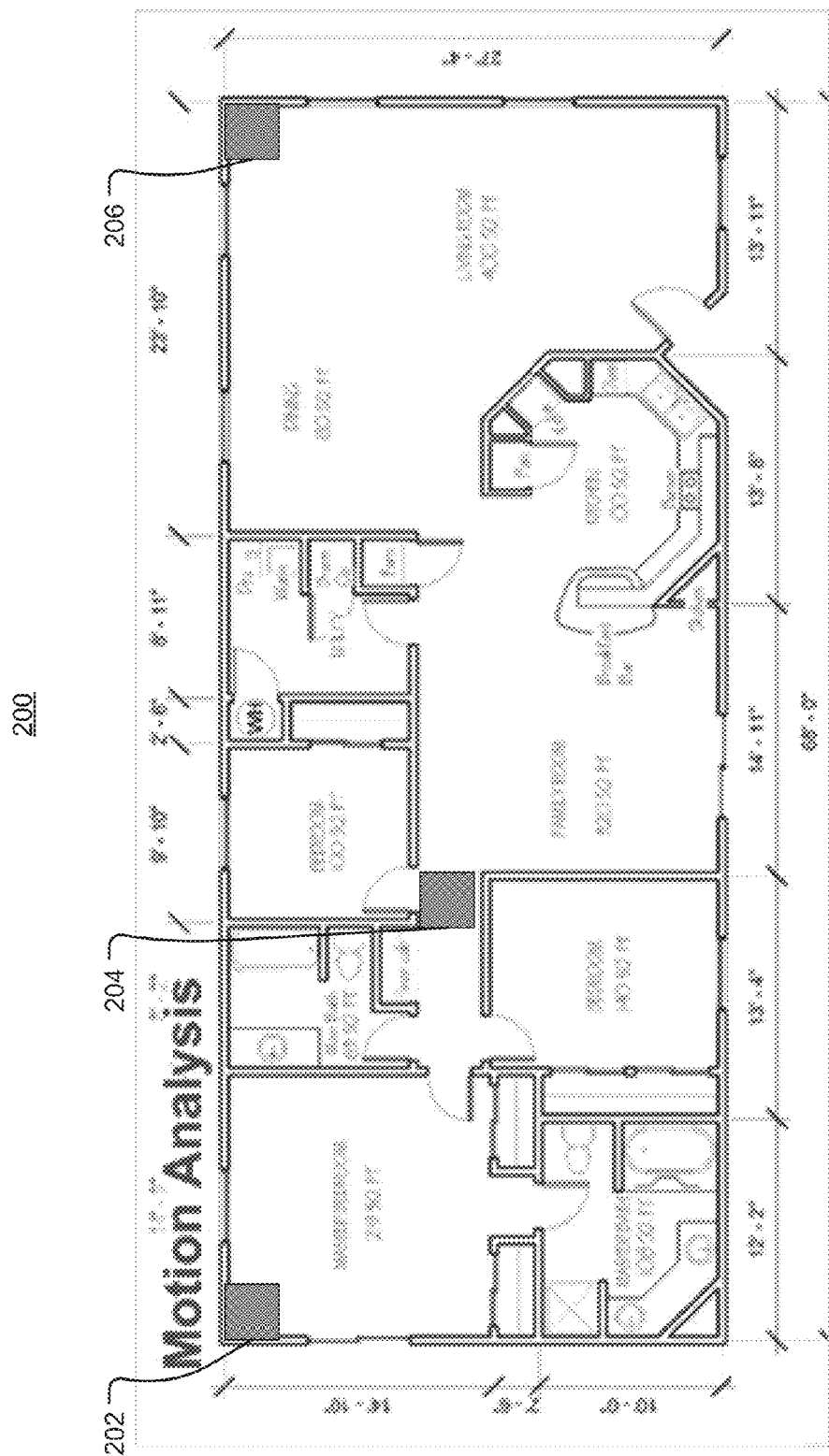
FIG. 2 is an illustration of a home environment configured for motion analysis, according to embodiments.

FIG. 2 is an illustration of a home environment 200 configured for motion analysis, consistent with embodiments of the present disclosure. Aspects of FIG. 2 are directed toward using one or more motion detecting (similarly referred to herein as motion sensing) devices 202, 204, 206 to collect environment data about one or more areas and identify a change in the home environment for a visually impaired user. As described herein, in certain embodiments, the home environment 200 may be a house, apartment, townhome, condominium, or other residence. The home environment 200 may include one or more areas, including a master bedroom, additional bedrooms, a family room, dining room, living room, kitchen, and multiple bathrooms. Other areas are also possible. As shown in FIG. 2, the motion sensing devices 202, 204, 206 may be located throughout the home environment 200. For example, in certain embodiments, the motion sensing device 202 may be located in the master bedroom, the motion sensing device 204 may be located in a hallway, and the motion sensing device 206 may be located in the living room of the home environment 200. Consistent with embodiments of the present disclosure, the motion sensing devices 202, 204, 206 may be household appliances configured for sound capture, such as televisions, radios, webcams, security systems, stereos, computers, mobile devices, and the like.

Aspects of the present disclosure, in certain embodiments, are directed toward a home environment 200 equipped with one or more motion sensing devices 202, 204, 206 configured to collect environmental data about one or more areas of the home environment, and identify a change in the home environment for a visually impaired user. The motion sensing devices 202, 204, 206 may be one or a combination of multiple different implementations. For example, the motion sensing devices 202, 204, 206 may include passive and active infrared sensors, optics sensors (e.g., video and camera systems), radio frequency systems (e.g., radar, microwave, and tomographic motion detection), sound (e.g. microphones and acoustic sensors), vibration (triboelectric, seismic, and inertia-switch sensors), magnetism-based sensors (e.g., magnetic sensors and magnetometers) and the like.

Consistent with various embodiments, the motion sensing devices 202, 204, 206 may be configured to monitor and record the time and location of motion that occurs within the home environment 200. Consider the following example. In certain embodiments, a user (e.g., a visually impaired user) may depart the home environment 200 in the morning when he or she leaves for work. While the user is out, the breeze through an open window may tip over a coat rack nearby the entrance to the home environment, causing it fall in front of the entrance. Accordingly, one or more of the motion sensing devices 202, 204, 206 may detect that the coat rack has fallen. In certain embodiments (described herein) the user may be notified that the coat rack has fallen, and be careful of the coat rack when he or she returns home. Although three motion sensing devices are depicted herein, greater or lesser numbers of motion sensing devices are also possible.

In certain embodiments, the motion sensing devices 202, 204, 206 may be configured to only monitor for movement during certain times of the day. For example, the motion sensing devices 202, 204, 206 may be equipped to monitor the home environment between the hours of 9 AM and 5 PM, while a visually impaired user is at work. In certain embodiments, the motion sensing devices 202, 204, 206 may be configured to monitor particular subsections of an area, such as in front of a door or nearby a table. In certain embodiments, the motion sensing devices 202, 204, 206 may be configured to monitor above or below a particular height threshold. For example, in certain embodiments, the motion sensing devices 202, 204, 206 may be configured to monitor for motion above a height of 1 meter from the floor. Such a configuration may, for instance, be useful for home environments with pets or small children.

Figure 3:
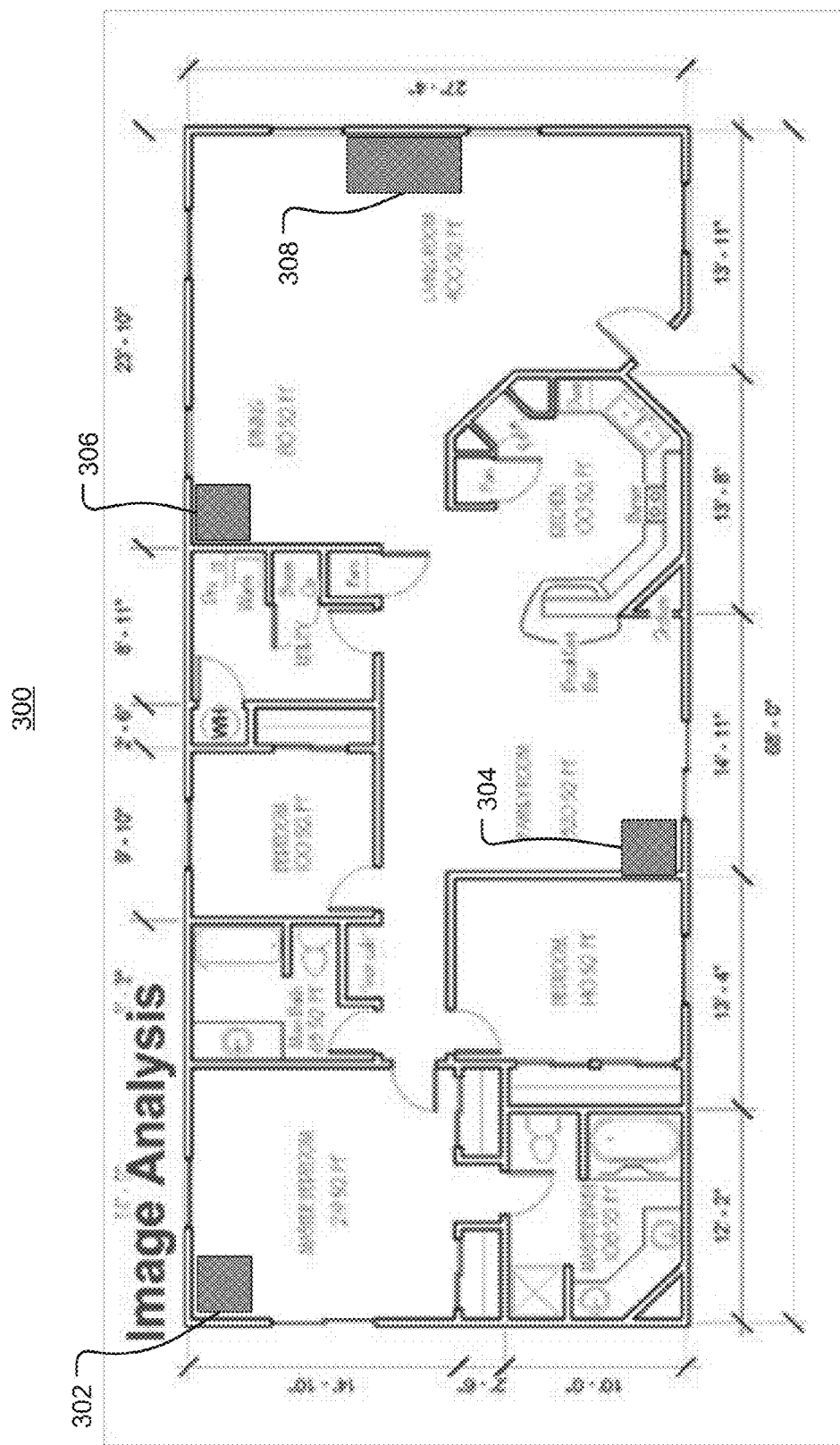
FIG. 3 is an illustration of a home environment configured for image analysis, according to embodiments.

FIG. 3 is an illustration of a home environment 300 configured for image analysis, consistent with embodiments of the present disclosure. Aspects of FIG. 3 are directed toward using one or more image capture devices 302, 304, 306, 308 to collect environment data about one or more areas and identify a change in the home environment for a visually impaired user. As described herein, in certain embodiments, the home environment 300 may be a house, apartment, townhome, condominium, or other residence. The home environment 300 may include one or more areas, including a master bedroom, additional bedrooms, a family room, dining room, living room, kitchen, and multiple bathrooms. Other areas are also possible. As shown in FIG. 3, the image capture devices 302, 304, 306, 308 may be located throughout the home environment 300. For example, in certain embodiments, the image capture device 302 may be located in the master bedroom, the image capture device 304 may be located in the family room, the image capture device 306 may be located in the dining room, and the image capture device 308 may be located in the living room of the home environment 300. Consistent with embodiments of the present disclosure, the image capture devices 302, 304, 306, 308 may be household appliances configured for sound capture, such as televisions, radios, webcams, security systems, stereos, computers, mobile devices, and the like.

Aspects of the present disclosure, in certain embodiments, are directed toward a home environment 300 equipped with one or more image capture devices 302, 304, 306, 308 configured to collect environmental data about one or more areas of the home environment, and identify a change in the home environment for a visually impaired user. The image capture devices 302, 304, 306, 308 may be one or a combination of multiple different implementations. For example, the image capture devices 302, 304, 306, 308 may include cameras capable of capturing still images as well as videos of the home environment 300. The images and video captured by the image capture devices 302, 304, 306, 308 may be maintained on local storage devices or on remote storage devices (e.g., the cloud, etc.) communicatively connected with the image capture devices 302, 304, 306, 308.

Consistent with various embodiments, the image capture devices 302, 304, 306, 308 may be configured to collect environment data including a first set of images of one or more areas of the home environment 300. The first set of images may serve as a "baseline" of the home environment 300, or a reference for use in identifying a change in the home environment 300. As an example, the image capture devices 302, 304, 306, 308 may capture a first set of images of the master bedroom, family room, dining room, and living room. In certain embodiments, the image capture devices 302, 304, 306, 308 may be communicatively connected to the motion capturing devices 202, 204, 206 described in FIG. 2. Accordingly, in certain embodiments, in response to receiving a motion alert from one or more of the motion capturing devices 202, 204, 206 of FIG. 2, the image capture devices 302, 304, 306, 308 may be configured to capture a second set of images for the set of areas of the home environment 300. The motion alert from the motion capturing devices 202, 204, 206 may be a notification of motion detected in one or more areas of the home environment 300. The second set of images may be configured to capture the same areas of the home environment 300 as captured by the first set of images.

In certain embodiments, the image capture devices 302, 304, 306, 308 can be configured to utilize digital image processing techniques to analyze the first set of images and the second set of images in order to identify a change (e.g., an object) of the second set of images meeting an obstruction criteria. In certain embodiments, identifying the object in the second set of images meeting the obstruction criteria may include using a digital image processing algorithm. The digital image processing algorithm can compare the first set of images with the second set of images, and use one or more object recognition techniques to identify the object in the second set of images. A variety of object recognition techniques are possible. For example, the digital image processing algorithm may use edge matching (e.g., Carny edge detection), greyscale matching, gradient matching, feature based methods, geometric hashing, Speeded Up Robust Features (SURF) techniques, and the like. In certain embodiments, the digital image processing algorithm may use Scale-Invariant Feature Transform (SIFT) to identify the image. Accordingly, the SIFT technique can use one or more "training images" to extract features descriptions of various objects, and match features of the object in the second set of images with the feature descriptions of the objects in the training images to identify the object.

Consider the following example. The SIFT technique may use training images of potted plants, packages, chairs, coat racks, desks, and other objects to identify feature descriptions such as the dimensions, shape, light reflective properties (e.g., response to illumination changes), and other key points for each object of the training images. Accordingly, in embodiments of the present disclosure, the SIFT technique may identify an object by comparing the first set of images to the second set of images, and determining that an object in the second set of images was not present in the first set of images, and matches the feature description of a known object.

As described herein, in certain embodiments, the object of the second set of images may meet an obstruction criteria. The digital image processing technique can include determining whether a given object in the set of images meets the obstruction technique. The obstruction criteria may include one or more factors that indicate that the object may be a potential obstacle or hazard for a user (e.g., a visually impaired user) traversing the area in which the object is located. In certain embodiments, the obstruction criteria can include a displacement threshold and an object size threshold. The obstruction criteria may be fulfilled if an object meets either the displacement threshold or the object size threshold. The displacement threshold may be a distance that an object has moved between an origin position of the first set of images and a subsequent position in the second set of images. For example, in certain embodiments, the displacement threshold may be 20 centimeters. Accordingly, an object in the second set of images that has moved less than 20 centimeters from its origin position in the first set of images may not meet the obstruction criteria, while an object in the second set of images that has moved more than 20 centimeters from its original position in the first set of images may meet the obstruction criteria.

In certain embodiments, the object size threshold may be a set of dimensions. In certain embodiments, the object size threshold may include a length threshold, width threshold, and height threshold. An object that exceeds either the length threshold, width threshold, or height threshold may meet the obstruction criteria. As an example, in certain embodiments, the object size threshold may be a length of 10 centimeters, a width of 10 centimeters, and a height of 30 centimeters. Accordingly, a potted plant that is 8 centimeters long, 8 centimeters wide, and 32 centimeters tall may meet the obstruction criteria. Although an object size threshold and a displacement threshold are specifically mentioned herein, other obstruction criteria (e.g., a temperature threshold, etc.) are also possible. In certain embodiments, the obstruction criteria can be managed by a mobile device. For example, the mobile device can include a set of preferences that allow a user to define the displacement threshold and the object size threshold.

Consistent with various embodiments, in response to a triggering event, the image capture devices 302, 304, 306, 308 can be configured to provide a notification of the object. Consistent with various embodiments, the notification of the object can be provided in one of a number of ways. For example, in certain embodiments, the notification of the object may be provided in the form of a voice message delivered via a mobile device, (e.g., smart phone, smart watch, tablet, etc.) or wearable computing device of the user. In certain embodiments, the mobile device of the user may vibrate or make a noise to indicate that an object meeting the obstruction criteria has been identified in one or more areas of the home environment 300. In certain embodiments, the notification may be a voice message that is announced in one or more areas of the home environment 300 via a speaker, intercom, stereo, television, radio, or other device. In certain embodiments, the notification of the object meeting the obstruction criteria may be provided as voice message announced through a dog collar equipped with a speaker and communicatively connected to the image capturing system. Other methods of providing the notification of the object meeting the obstruction criteria are also possible.

Consistent with various embodiments, the triggering event can be one of a number of different occurrences, triggers, or stimuli that can be detected by the sensors or other method. In certain embodiments, the triggering event may be a home arrival (e.g., of a user). The home arrival may be detected in one of a number of ways. In certain embodiments, the home arrival may be detected by a security system of the home environment 300 in response to a door unlock, or the opening of a garage door. For example, when a user arrives home, he or she may insert a key into a door of the home environment 300. Accordingly, this action may be detected by a security system of the home environment 300, and the user may be provided with a notification of the object meeting the obstruction criteria.

Aspects of the present disclosure, in certain embodiments, relate to the recognition that visually impaired users may keep a dog or other pet trained to assist them. Accordingly, in certain embodiments, the home arrival of the user may be detected based on detection of a dog barking. In certain embodiments, the home environment may be equipped with a sound capture device, such as a microphone, configured to record a set of dog barks. In response to recording the set of dog barks, the sound capture device or other system may analyze the bark frequency and the bark pitch of the set of dog barks. The bark frequency and the bark pitch may vary based on the individual who has arrived at the home. For instance, for an unknown individual, the bark pitch may generally be lower (e.g., to intimidate an unknown individual), while, for a recognized individual, the bark pitch may be higher. Additionally, bark frequency may be greater for an unknown individual than for a known individual. In certain embodiments, the barking habits of a particular dog in response to known individuals and unknown individuals may be recorded and analyzed to create a baseline bark profile. Accordingly, the bark pitch and bark frequency of the set of dog barks can be compared to the baseline bark profile to indicate whether it is likely that the home arrival is a known user or an unknown user. In response to determining that the bark pitch and bark frequency indicate a home arrival of a known user, the notification of the object meeting the obstruction criteria may be provided to the user. Although bark pitch and bark frequency are specifically referenced herein, other bark features are also contemplated.

In certain embodiments, the triggering event may be an area transition. The area transition may, in certain embodiments, a user moving from one area of the home environment 300 to another area of the home environment 300. For example, the area transition may include a user moving from the dining room to the living room. Aspects of the present disclosure, in certain embodiments, relate to the recognition that visually impaired users may make use of a cane, walker, or other assistive device to navigate the areas of the home environment 300. Accordingly, in certain embodiments, the area transition may be detected by a radio-frequency identification (RFID) tracking system configured to monitor the location of a cane (or other assistive device) of the user. In certain embodiments, the cane of the user may be equipped with an RFID bit communicatively connected to the RFID tracking system. In certain embodiments, the RFID tracking system can be configured to detect that the location of the cane of the user has been displaced by a distance value greater than a distance threshold. Consider the following example. In certain embodiments, the distance threshold may be set to 3 meters. A user may walk, using his or her cane, from the master bedroom to the family room of the home environment 300, traveling a distance of 7 meters. The RFID tracking system may detect that the location of the cane has moved by a distance of 7 meters, greater than the distance threshold of 3 meters. Accordingly, notification of the object meeting the obstruction criteria may be provided to the user.

In certain embodiments, the area transition may be detected by a thermal imaging system configured to monitor a body heat signature. The thermal imaging system may include one or more thermal cameras located throughout the home environment 300. In certain embodiments, the body heat signature may be that of a visually impaired user. In certain embodiments, the body heat signature may be that of a dog or other pet of the visually impaired user. The thermal imaging system may be configured to detect that the body heat signature has been displaced by a distance value greater than a distance threshold. For instance, in certain embodiments, the distance threshold may be set to 1.5 meters. A user may walk from the kitchen to the living room of the home environment 300, traveling a distance of 3 meters. The thermal imaging system may detect that the body heat signature of the user has moved by a distance of 3 meters, greater than the distance threshold of 1.5 meters. Accordingly, notification of the object meeting the obstruction criteria may be provided to the user.

Consider the following example. A visually impaired user may be relaxing by watching television in the living room of the home environment 300. A faithful guide dog named Toby may be resting comfortably nearby the visually impaired user. While the user is watching TV, a picture frame hanging on the wall in the hallway may fall because the fastener holding it to the wall broke. Due to the noise of the television, the user may not have heard the sound of the picture frame falling. In certain embodiments, the image capturing device 304 may capture an image of the hallway (e.g., a second set of images) and compare the image with a baseline set of images taken at a previous time. The image capturing device 304 may use a digital image processing algorithm and object recognition techniques to identify that the picture frame was not lying on the floor in the baseline set of images. The image capturing device 304 may further determine that the picture frame measures 80 centimeters by 100 centimeters by 5 centimeters, larger than an object size threshold of 15 centimeters by 15 centimeters by 15 centimeters. At some time later, the user may rise to go use the bathroom, and begin walking out of the living room. The distance threshold may be 2.5 meters. When the user surpasses the distance threshold of 2.5 meters from his original position, the image capturing system may send a message notifying the user of the obstacle in the hallway. The message may be provided as a voice message played through a speaker in the collar of the faithful guide dog named Toby.

Figure 4:
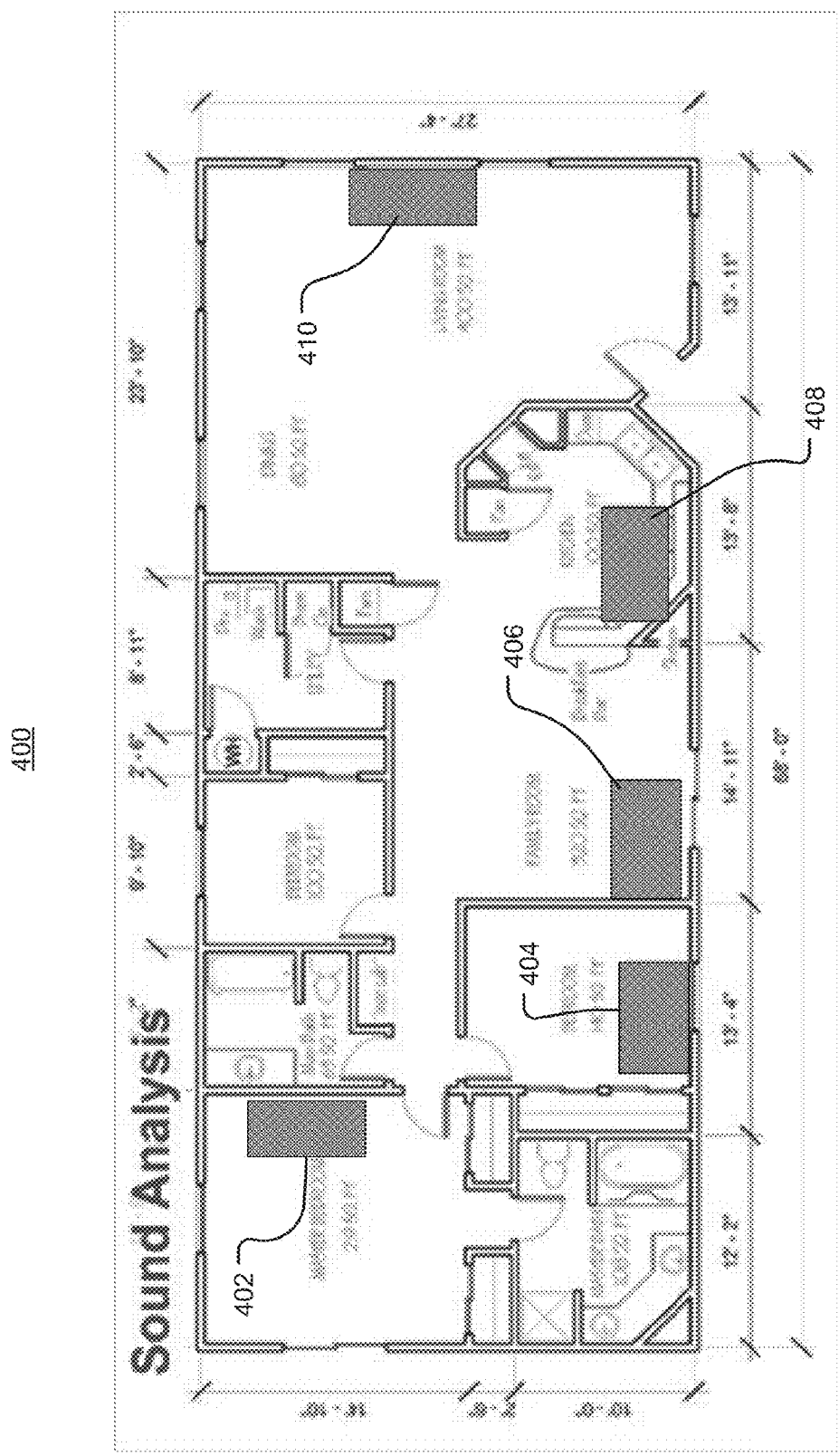
FIG. 4 is an illustration of a home environment configured for sound analysis, according to embodiments.

FIG. 4 is an illustration of a home environment 400 configured for sound analysis, consistent with embodiments of the present disclosure. Aspects of FIG. 4 are directed toward using one or more sound capture devices 402, 404, 406, 408, 410 to collect environment data about one or more areas and identify a change in the home environment for a visually impaired user. As described herein, in certain embodiments, the home environment 400 may be a house, apartment, townhome, condominium, or other residence. The home environment 400 may include one or more areas, including a master bedroom, additional bedrooms, a family room, dining room, living room, kitchen, and multiple bathrooms. Other areas are also possible. As shown in FIG. 4, the sound capture devices 402, 404, 406, 408, 410 may be located throughout the home environment 400. For example, in certain embodiments, the sound capture device 402 may be located in the master bedroom, the sound capture device 404 may be located in a bedroom, the sound capture device 406 may be located in the family room, the sound capture device 408 may be located in the kitchen, and the sound capture device 410 may be located in the living room. Consistent with embodiments of the present disclosure, the sound capture devices 402, 404, 406, 408, 410 may be household appliances configured for sound capture, such as televisions, radios, webcams, security systems, stereos, computers, mobile devices, and the like.

Aspects of the present disclosure, in certain embodiments, are directed toward a home environment 400 equipped with one or more sound capture devices 402, 404, 406, 408, 410 configured to collect environmental data about one or more areas of the home environment, and identify a change in the home environment for a visually impaired user. The sound capture devices 402, 404, 406, 408, 410 may be one or a combination of multiple different implementations. For example, the sound capture devices 402, 404, 406, 408, 410 may include microphones capable of receiving and recording audio data such as sound waves. The audio data captured by the sound capture devices 402, 404, 406, 408, 410 may be maintained on local storage devices or on remote storage devices (e.g., the cloud) communicatively connected with the sound capture devices 402, 404, 406, 408, 410.

Consistent with various embodiments of the present disclosure, the sound capture devices 402, 404, 406, 408, 410 may be configured to collect environment data in the form of a first sonar map of the areas of the home environment 400. The first sonar map may serve as a "baseline" of the home environment 400, Consistent with various embodiments, the sound capture devices 402, 404, 406, 408, 410 may be configured to collect environment data including a first sonar map of one or more areas of the home environment 400. The first sonar map may serve as a "baseline" of the home environment 400, or a reference for use in identifying a change in the home environment 400. The first sonar map may capture architectural features (e.g., the location of walls, doors) as well as objects (e.g., furniture, appliances). As an example, the image capture devices sound capture devices 402, 404, 406, 408, 410 may capture a first sonar map of the master bedroom, family room, dining room, and living room. In certain embodiments, the sound capture devices 402, 404, 406, 408, 410 may be communicatively connected to the motion capturing devices 202, 204, 206 described in FIG. 2. Accordingly, in certain embodiments, in response to receiving a motion alert from one or more of the motion capturing devices 202, 204, 206 of FIG. 2, the sound capture devices 402, 404, 406, 408, 410 may be configured to capture a second sonar map for the set of areas of the home environment 400. The motion alert from the motion capturing devices 202, 204, 206 may be a notification of motion detected in one or more areas of the home environment 400. The second sonar map may be configured to capture the same areas of the home environment 400 as captured by the first sonar map.

The first sonar map and the second sonar map may be captured in one of a number of ways. In certain embodiments, capturing the first and second sonar map can include emitting a sound probe by the sound capture devices 402, 404, 406, 408, 410. The sound capture devices 402, 404, 406, 408, 410 can then listen for sound waves reflected from the furniture, walls, and other features of the home environment 400 in response to the sound probe, and use the reflected sound waves to create a three-dimensional sonar map of the features of the home environment 400. In certain embodiments, multiple sound probes may be emitted by the sound capture devices 402, 404, 406, 408, 410. In certain embodiments, the sound capture devices 402, 404, 406, 408, 410 may be configured to collect a background noise level of the home environment 400. The background noise level may include noises such as conversation, the sound of a television, radio, or computer, fan, or the like. In certain embodiments, the background noise level may be distinguished from the sound waves received in response to the sound probe based on frequency and wavelength differences. Accordingly, the background noise level may not be used in creating the first and second sonar map.

Consistent with various embodiments of the present disclosure, the sound capture devices 402, 404, 406, 408, 410 can be configured to compare the first sonar map and the second sonar map to one another to identify an environmental change in the home environment 400 (e.g., an object present in the second sonar map that was not present in the first sonar map). In certain embodiments, the sound capture devices 402, 404, 406, 408, 410 can use digital image processing techniques similar to those used by the image capture devices 302, 304, 306, 308 of FIG. 3. In certain embodiments, the sound capture devices 402, 404, 406, 408, 410 may be configured to identify an object meeting an obstruction threshold. As described herein, the object threshold may include an object displacement threshold based on an origin position and a subsequent position of the object, and an object size threshold based on a measurement of the length, width, and height of the object.

In certain embodiments, in response to a triggering event, the sound capture devices 402, 404, 406, 408, 410 can be configured to provide a notification of the object meeting the obstruction criteria. In certain embodiments, the sound capture devices 402, 404, 406, 408, 410 can be configured to provide the notification using techniques and methods similar to those used by the image capture devices 302, 304, 306, 308 of FIG. 3. For example, the notification of the object may be provided to the visually impaired user as a voice message announced through a mobile device, or over an intercom or speaker system of the home environment 400. In certain embodiments, the notification of the object may be provided through a particular household device that the user is in close proximity with (e.g., through the speakers of a television that the user is watching.) The proximity of a user to a particular household device may be determined by an RFID tracking system or by a thermal imaging system, as described herein.

In certain embodiments, the triggering event may be a signal or an alert from a sleep sensor configured to monitor the sleep cycle of a user. As an example, in certain embodiments, the triggering event may include detecting, by the sleep sensor, that a user has awakened from sleeping. The sleep sensor may be configured to monitor one or more biological signs of the user, such as heart rate, respiration frequency, neural behavior, eye movement, snoring, and the like. For example, the sleep sensor may determine that a user has awoken based on a pulse (70 beats per minute) that has increased beyond a pulse threshold (65 beats per minute), or a respiration frequency (14 breaths per minute) that has increased beyond a respiration threshold (12 breaths per minute). The pulse threshold and the respiration threshold may be determined by the sleep sensor based on typical sleeping heart rate and respiration rate data of the user. Consider the following example. A user may be sleeping in a bedroom of the home environment 400. While the user is sleeping, another inhabitant of the home environment may move a chair in the kitchen to reach a cookie jar on top of the refrigerator before retiring to his or her room, without replacing the kitchen chair. The sound capture devices 402, 404, 406, 408, 410 may detect the new position of the chair by comparing a first sonar map to a second sonar map, and determining that the chair meets an obstruction criteria (e.g., a displacement of more than 50 centimeters from its origin position). Accordingly, in response to determining that the user has awoken, the sound capture devices 402, 404, 406, 408, 410 can provide the user with a notification of the obstruction.

Figure 5:
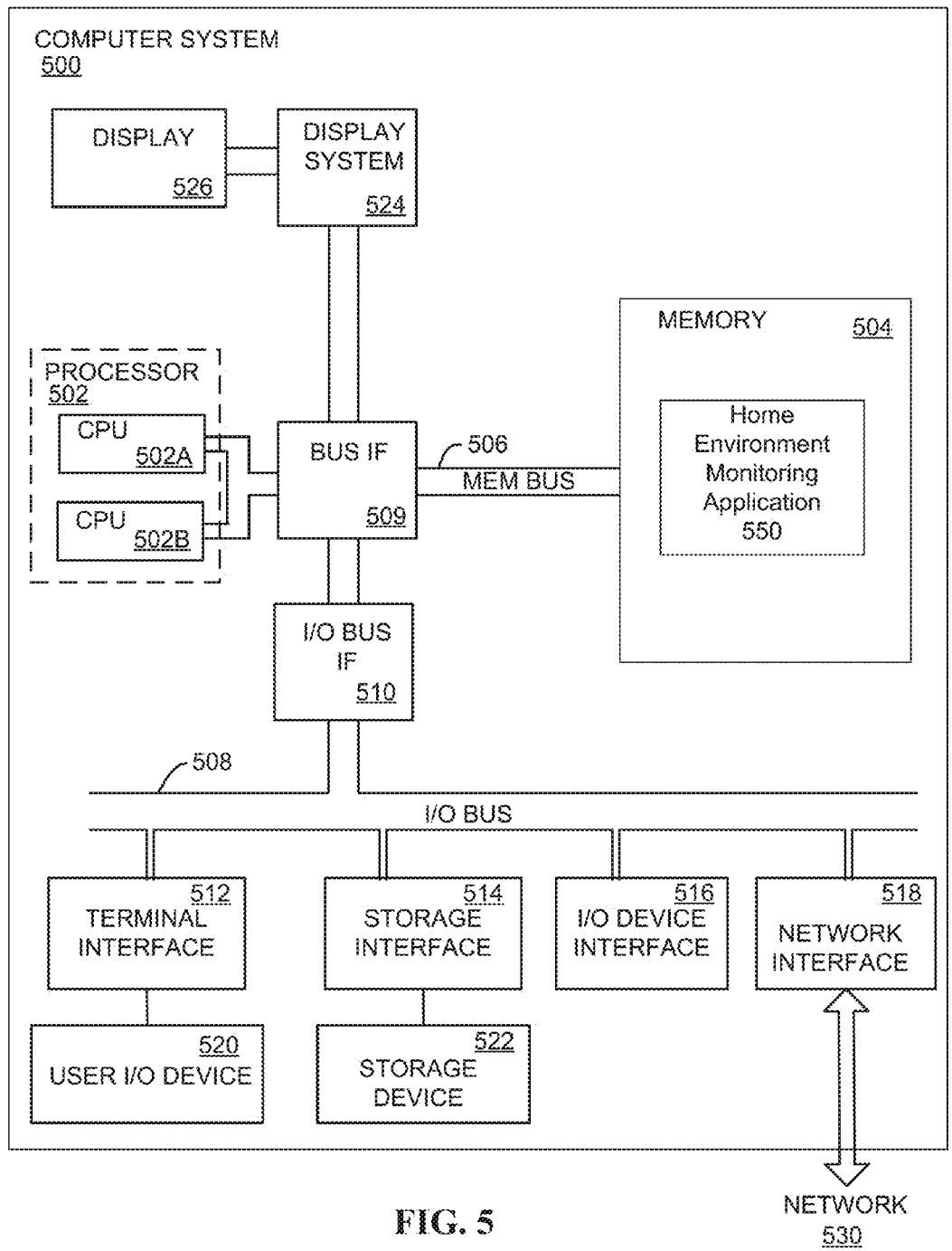
FIG. 5 depicts a high-level block diagram of a computer system for implementing various embodiments, according to embodiments.

FIG. 5 depicts a high-level block diagram of a computer system 500 for implementing various embodiments. The mechanisms and apparatus of the various embodiments disclosed herein apply equally to any appropriate computing system. The major components of the computer system 500 include one or more processors 502, a memory 504, a terminal interface 512, a storage interface 514, an I/O (Input/Output) device interface 516, and a network interface 518, all of which are communicatively coupled, directly or indirectly, for inter-component communication via a memory bus 506, an I/O bus 508, bus interface unit 509, and an I/O bus interface unit 510.

The computer system 500 may contain one or more general-purpose programmable central processing units (CPUs) 502A and 502B, herein generically referred to as the processor 502. In embodiments, the computer system 500 may contain multiple processors; however, in certain embodiments, the computer system 500 may alternatively be a single CPU system. Each processor 502 executes instructions stored in the memory 504 and may include one or more levels of on-board cache.

In embodiments, the memory 504 may include a random-access semiconductor memory, storage device, or storage medium (either volatile or non-volatile) for storing or encoding data and programs. In certain embodiments, the memory 504 represents the entire virtual memory of the computer system 500, and may also include the virtual memory of other computer systems coupled to the computer system 500 or connected via a network. The memory 504 can be conceptually viewed as a single monolithic entity, but in other embodiments the memory 504 is a more complex arrangement, such as a hierarchy of caches and other memory devices. For example, memory may exist in multiple levels of caches, and these caches may be further divided by function, so that one cache holds instructions while another holds non-instruction data, which is used by the processor or processors. Memory may be further distributed and associated with different CPUs or sets of CPUs, as is known in any of various so-called non-uniform memory access (NUMA) computer architectures.

The memory 504 may store all or a portion of the various programs, modules and data structures for processing data transfers as discussed herein. For instance, the memory 504 can store a home environment monitoring application 550. In embodiments, home environment monitoring application 550 may include instructions or statements that execute on the processor 502 or instructions or statements that are interpreted by instructions or statements that execute on the processor 502 to carry out the functions as further described below. In certain embodiments, the home environment monitoring application 550 is implemented in hardware via semiconductor devices, chips, logical gates, circuits, circuit cards, and/or other physical hardware devices in lieu of, or in addition to, a processor-based system. In embodiments, the home environment monitoring application 550 may include data in addition to instructions or statements.

The computer system 500 may include a bus interface unit 509 to handle communications among the processor 502, the memory 504, a display system 524, and the I/O bus interface unit 510. The I/O bus interface unit 510 may be coupled with the I/O bus 508 for transferring data to and from the various I/O units. The I/O bus interface unit 510 communicates with multiple I/O interface units 512, 514, 516, and 518, which are also known as I/O processors (IOPs) or I/O adapters (IOAs), through the I/O bus 508. The display system 524 may include a display controller, a display memory, or both. The display controller may provide video, audio, or both types of data to a display device 526. The display memory may be a dedicated memory for buffering video data. The display system 524 may be coupled with a display device 526, such as a standalone display screen, computer monitor, television, or a tablet or handheld device display. In one embodiment, the display device 526 may include one or more speakers for rendering audio. Alternatively, one or more speakers for rendering audio may be coupled with an I/O interface unit. In alternate embodiments, one or more of the functions provided by the display system 524 may be on board an integrated circuit that also includes the processor 502. In addition, one or more of the functions provided by the bus interface unit 509 may be on board an integrated circuit that also includes the processor 502.

The I/O interface units support communication with a variety of storage and I/O devices. For example, the terminal interface unit 512 supports the attachment of one or more user I/O devices 520, which may include user output devices (such as a video display device, speaker, and/or television set) and user input devices (such as a keyboard, mouse, keypad, touchpad, trackball, buttons, light pen, or other pointing device). A user may manipulate the user input devices using a user interface, in order to provide input data and commands to the user I/O device 520 and the computer system 500, and may receive output data via the user output devices. For example, a user interface may be presented via the user I/O device 520, such as displayed on a display device, played via a speaker, or printed via a printer.

The storage interface 514 supports the attachment of one or more disk drives or direct access storage devices 522 (which are typically rotating magnetic disk drive storage devices, although they could alternatively be other storage devices, including arrays of disk drives configured to appear as a single large storage device to a host computer, or solid-state drives, such as flash memory). In some embodiments, the storage device 522 may be implemented via any type of secondary storage device. The contents of the memory 504, or any portion thereof, may be stored to and retrieved from the storage device 522 as needed. The I/O device interface 516 provides an interface to any of various other I/O devices or devices of other types, such as printers or fax machines. The network interface 518 provides one or more communication paths from the computer system 500 to other digital devices and computer systems; these communication paths may include, e.g., one or more networks 530.

Although the computer system 500 shown in FIG. 5 illustrates a particular bus structure providing a direct communication path among the processors 502, the memory 504, the bus interface 509, the display system 524, and the I/O bus interface unit 510, in alternative embodiments the computer system 500 may include different buses or communication paths, which may be arranged in any of various forms, such as point-to-point links in hierarchical, star or web configurations, multiple hierarchical buses, parallel and redundant paths, or any other appropriate type of configuration. Furthermore, while the I/O bus interface unit 510 and the I/O bus 508 are shown as single respective units, the computer system 500 may, in fact, contain multiple I/O bus interface units 510 and/or multiple I/O buses 508. While multiple I/O interface units are shown, which separate the I/O bus 508 from various communications paths running to the various I/O devices, in other embodiments, some or all of the I/O devices are connected directly to one or more system I/O buses.

In various embodiments, the computer system 500 is a multi-user mainframe computer system, a single-user system, or a server computer or similar device that has little or no direct user interface, but receives requests from other computer systems (clients). In other embodiments, the computer system 500 may be implemented as a desktop computer, portable computer, laptop or notebook computer, tablet computer, pocket computer, telephone, smart phone, or any other suitable type of electronic device.

FIG. 5 depicts several major components of the computer system 500. Individual components, however, may have greater complexity than represented in FIG. 5, components other than or in addition to those shown in FIG. 5 may be present, and the number, type, and configuration of such components may vary. Several particular examples of additional complexity or additional variations are disclosed herein; these are by way of example only and are not necessarily the only such variations. The various program components illustrated in FIG. 5 may be implemented, in various embodiments, in a number of different manners, including using various computer applications, routines, components, programs, objects, modules, data structures, etc., which may be referred to herein as "software," "computer programs," or simply "programs."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

What is claimed is:

1. A computer implemented method for detecting a change in a home environment for a visually impaired user, the method comprising:
   monitoring the home environment using a set of sensors configured to collect environment data for a set of areas of the home environment;
   detecting an environmental change in an area of the home environment; and
   providing, in response to a triggering event, a notification of the environmental change;
   wherein collecting the environment data includes capturing, by an image capturing system, a first set of images for the set of areas of the home environment;
   wherein detecting the environmental change in the area of the home environment includes:
      capturing, in response to receiving a motion alert from a motion detection system coupled to the image capturing system, a second set of images for the set of areas, and
      identifying an object of the second set of images meeting an obstruction criteria;
   wherein providing the notification of the environmental change includes notifying a user, using a mobile device communicatively connected to the image capturing system, of the identified object meeting the obstruction criteria in response to detecting a home arrival;
   wherein detecting the home arrival further comprises:
      recording, by a sound capture device, a set of dog barks;
      analyzing, in response to recording the set of dog barks, a bark frequency and a bark pitch of the set of dog barks; and
      determining, based on the bark frequency and the bark pitch, occurrence of the home arrival.

2. The method of claim 1, wherein the set of sensors includes one or more selected from the group consisting of motion sensors, audio sensors, or cameras.

3. The method of claim 1, wherein the obstruction criteria includes an object displacement threshold based on an origin position and a subsequent position, and an object size threshold based on a first dimension, a second dimension, and a third dimension.

4. The method of claim 1, wherein the home arrival is detected by a security system in response to a door unlock of a home.

5. The method of claim 1, wherein:
   collecting the environment data includes capturing, by an image capturing system, a first set of images for the set of areas of the home environment;
   detecting the environmental change in the area of the home environment includes:
      capturing, in response to receiving a motion alert from a motion detection system coupled to the image capturing system, a second set of images for the set of areas, and
      identifying an object of the second set of images meeting an obstruction criteria; and
   providing the notification of the environmental change includes notifying a user, using a mobile device communicatively connected to the image capturing system, of the identified object meeting the obstruction criteria in response to detecting an area transition.

6. The method of claim 5, wherein detecting the area transition further comprises:
   monitoring, using a radio-frequency identification (RFID) tracking system, the location of a cane of the user, wherein the cane is equipped with a RFID bit communicatively connected to the RFID tracking system;
detecting that the location of the cane has been displaced by a distance value greater than a distance threshold.

7. The method of claim 5, wherein detecting the area transition further comprises:
monitoring, using a thermal imaging system, a body heat signature; and
detecting that the body heat signature has been displaced by a distance value greater than a distance threshold.

8. The method of claim 5, wherein providing the notification of the environmental change includes announcing, through a dog collar communicatively connected to the image capturing system and equipped with a speaker, a voice message notifying the user of the identified object meeting the obstruction criteria.

9. A system for detecting a change in a home environment for a visually impaired user, the system comprising:
a monitoring module configured to monitor the home environment using a set of sensors configured to collect environment data for a set of areas of the home environment;
a detecting module configured to detect an environmental change in an area of the home environment; and
a providing module configured to provide, in response to a triggering event, a notification of the environmental change;
wherein collecting the environment data includes capturing, by an image capturing system, a first set of images for the set of areas of the home environment;
wherein detecting the environmental change in the area of the home environment includes:
a capturing module configured to capture, in response to receiving a motion alert from a motion detection system coupled to the image capturing system, a second set of images for the set of areas, and
an identifying module configured to identify an object of the second set of images meeting an obstruction criteria;
wherein providing the notification of the environmental change includes notifying a user, using a mobile device communicatively connected to the image capturing system, of the identified object meeting the obstruction criteria in response to detecting a home arrival; and
wherein detecting the home arrival further comprises:
recording, by a sound capture device, a set of dog barks;
an analyzing module configured to analyze, in response to recording the set of dog barks, a bark frequency and a bark pitch of the set of dog barks; and
a determining module configured to determine, based on the bark frequency and the bark pitch, occurrence of the home arrival.

10. The system of claim 9, wherein the obstruction criteria includes an object displacement threshold based on an origin position and a subsequent position, and an object size threshold based on a first dimension, a second dimension, and a third dimension.

11. A computer program product comprising a computer readable storage medium having a computer readable program stored therein, wherein the computer readable program, when executed on a first computing device, causes the first computing device to:
monitor the home environment using a set of sensors configured to collect environment data for a set of areas of the home environment;
detect an environmental change in an area of the home environment; and
provide, in response to a triggering event, a notification of the environmental change,
wherein the environment data includes a first set of images for the set of areas of the home environment captured by an image capturing system;
wherein the computer readable program is further configured to cause the first computing device to detect the environmental change in the area of the home environment by identifying an object of a second set of images meeting an obstruction criteria, the second set of images captured in response to receiving a motion alert from a motion detection system coupled to the image capturing system;
wherein the computer readable program is further configured to cause the first computing device to provide the notification of the environmental change includes by notifying a user, using a mobile device communicatively connected to the image capturing system, of the identified object meeting the obstruction criteria in response to detecting a home arrival; and
wherein the computer readable program is configured to cause the first computing device to detect the home arrival by:
analyzing a bark frequency and a bark pitch of a set of dog barks recorded by a sound capture device; and
determining, based on the bark frequency and the bark pitch, occurrence of the home arrival.

\* \* \* \* \*